(12) United States Patent
Ettlin

(10) Patent No.: US 11,364,095 B2
(45) Date of Patent: Jun. 21, 2022

(54) DISCHARGER

(71) Applicant: medmix Switzerland AG, Haag (CH)

(72) Inventor: Josef Ettlin, Eichberg (CH)

(73) Assignee: MEDMIX SWITZERLAND AG, Haag (CH)

(*) Notice: Subject to any disclaimer, the term of this patent is extended or adjusted under 35 U.S.C. 154(b) by 814 days.

(21) Appl. No.: 16/065,375

(22) PCT Filed: Dec. 22, 2016

(86) PCT No.: PCT/EP2016/082470
§ 371 (c)(1),
(2) Date: Jun. 22, 2018

(87) PCT Pub. No.: WO2017/109125
PCT Pub. Date: Jun. 29, 2017

(65) Prior Publication Data
US 2021/0205539 A1 Jul. 8, 2021

(30) Foreign Application Priority Data

Dec. 23, 2015 (EP) .................................. 15202345

(51) Int. Cl.
*A61C 5/62* (2017.01)
*A61M 5/28* (2006.01)
*A61M 5/315* (2006.01)

(52) U.S. Cl.
CPC ............... *A61C 5/62* (2017.02); *A61M 5/283* (2013.01); *A61M 5/288* (2013.01); *A61M 5/31571* (2013.01)

(58) Field of Classification Search
CPC .. A61J 7/00; A61J 1/20; A61M 35/00; A61M 5/28; A61M 5/315; A61C 5/62
See application file for complete search history.

(56) References Cited

U.S. PATENT DOCUMENTS 2,408,323 A * 9/1946 Lockhart ............. A61M 5/2448
604/198
2,778,360 A * 1/1957 Miskel ................ A61M 5/2448
604/87
(Continued)

FOREIGN PATENT DOCUMENTS

EP 0959010 A1 11/1999
EP 1607343 A1 12/2005
(Continued)

OTHER PUBLICATIONS

International Preliminary Report on Patentability and Written Opinion dated Jun. 26, 2018 in corresponding International Application No. PCT/EP2016/082470, filed Dec. 22, 2016.
(Continued)

*Primary Examiner* — Scott J Medway
(74) *Attorney, Agent, or Firm* — Global IP Counselors, LLP

(57) ABSTRACT

A discharger for discharging a predetermined amount of fluid from a separate container including a discharge section defining a longitudinal axis and having a proximal end and a distal end and having a discharge passage for the fluid extending between an inlet opening and an outlet opening of the discharge section. The discharger further includes an intermediate section including a distal portion cooperating with the proximal end of the discharge section and a proximal portion defining a receiving space which is adapted to be loaded with the separate container holding an amount of fluid to be discharged by the discharger. The distal portion and the proximal portion are formed in one piece and are interconnected by a breakable section.

18 Claims, 3 Drawing Sheets

(56) References Cited

U.S. PATENT DOCUMENTS

| | | | | |
|---|---|---|---|---|
| 3,340,873 | A * | 9/1967 | Solowey | A61J 1/2093 604/87 |
| 3,946,732 | A * | 3/1976 | Hurscham | A61J 1/2093 604/88 |
| 3,965,898 | A | 6/1976 | Cloyd | |
| 4,060,082 | A * | 11/1977 | Lindberg | A61M 5/284 604/89 |
| 4,078,565 | A | 3/1978 | Genese | |
| 4,180,070 | A * | 12/1979 | Genese | A61J 1/2089 604/88 |
| 4,767,413 | A * | 8/1988 | Haber | A61M 5/326 604/232 |
| 4,927,414 | A * | 5/1990 | Kulli | A61M 5/3234 604/110 |
| 5,478,324 | A | 12/1995 | Meyer | |
| 5,788,677 | A * | 8/1998 | Botich | A61M 5/3234 604/195 |
| 6,159,184 | A * | 12/2000 | Perez | A61M 5/3271 604/234 |
| 6,620,134 | B1 | 9/2003 | Trombley, III et al. | |
| 7,329,235 | B2 | 2/2008 | Bertron et al. | |
| 7,488,307 | B2 * | 2/2009 | Rimlinger | A61M 5/5086 604/197 |
| 7,717,874 | B2 | 5/2010 | Landau et al. | |
| 8,632,493 | B2 * | 1/2014 | Cali | A61M 5/3234 604/110 |
| 8,721,602 | B2 | 5/2014 | Poveda Estepa | |
| 9,579,257 | B2 * | 2/2017 | Davidian | A61M 5/31586 |
| 10,220,147 | B2 * | 3/2019 | Constantineau | A61M 5/3243 |
| 2002/0169421 | A1 | 11/2002 | McWethy et al. | |
| 2009/0093757 | A1 | 4/2009 | Tennican | |
| 2015/0174006 | A1 | 6/2015 | Qiu et al. | |
| 2015/0209570 | A1 * | 7/2015 | Lee | F16F 1/3732 604/244 |
| 2019/0030257 | A1 * | 1/2019 | Tran | A61M 5/31591 |

FOREIGN PATENT DOCUMENTS

| | | | | |
|---|---|---|---|---|
| EP | 2905040 | A1 | 8/2015 | |
| FR | 2958548 | A1 * | 10/2011 | A61M 5/2466 |
| WO | 0172362 | A1 | 10/2001 | |
| WO | 2013149445 | A1 | 10/2013 | |

OTHER PUBLICATIONS

International Search Report dated Jun. 30, 2017 in corresponding International Application No. PCT/EP2016/082470, filed Dec. 22, 2016.

\* cited by examiner

DISCHARGER

CROSS-REFERENCE TO RELATED APPLICATION

This application is a U.S. National Stage application of International Application No. PCT/EP2016/082470, filed Dec. 22, 2016, which claims priority to EP Patent Application No. 15202345.3, filed Dec. 23, 2015, the contents of each of which are hereby incorporated herein by reference.

BACKGROUND

Field of the Invention

The present disclosure relates to a discharger, in particular expendable syringe, for discharging a predetermined amount of fluid, preferably from a separate container, in particular a liquid including at least one medical, dental or veterinary agent.

Background Information

In general, dischargers such as expendable syringes for use in the medical, dental or veterinary field are known which normally comprise a housing, a discharge passage, one or more compartments in which the medical, dental or veterinary agent or a liquid including the medical, dental or veterinary agent is contained before use and, where appropriate, a kind of plunger. In order to avoid spreading infectious diseases from one patient to another or to avoid energy-intensive cleaning processes such dischargers are usually provided as disposable articles, i.e. for single use only. Against the background of a most cost-efficient but also environmentally sound production it is desirable to keep material consumption as low as possible, however, without compromising user friendliness.

EP 2 905 040 A1 teaches a discharger in accordance with the preamble of claim 1. EP 0 959010 A1 and EP 1 607 343 A1 both disclose a cartridge having a breakable section that allows to open one end of the cartridge.

SUMMARY

It is an object of the present invention to provide a discharger for discharging a predetermined amount of fluid which is environment-friendly producible but which still enables an easy and reliable usage and which at the same time can be produced in large quantities at low cost.

These objects are satisfied by a discharger having the features described herein.

In accordance with the invention, a discharger, preferably expendable syringe, for discharging a predetermined amount of fluid, preferably from a separate container, in particular a liquid including at least one medical, dental or veterinary agent, comprises a discharge section defining a longitudinal axis and having a proximal end and a distal end and having a discharge passage for the fluid extending between an inlet opening and an outlet opening of the discharge section. The discharger further comprises an intermediate section comprising a distal portion cooperating with the proximal end of the discharge section and a proximal portion defining a receiving space which is adapted to be loaded with the separate container holding an amount of fluid to be discharged, preferably by the discharger. The distal portion and the proximal portion are formed in one piece and are interconnected by a breakable section.

The present disclosure is not limited to the medical, dental or veterinary sector and can be used in other appliances in which it is desirable to discharge a predetermined amount of fluid in a reliable and uniform manner. The present disclosure is also not limited to the discharge of fluids such as liquids. The discharger as disclosed herein may alternatively be adapted or used to discharge viscous or gel-like or even powdery or fine granular materials.

The breakable section of the intermediate section preferably can comprise a predetermined breaking area or breaking point adapted to break upon applying an axial force to the intermediate section, in particular along the longitudinal axis, especially towards the distal end of the discharge section.

Advantageously, the force upon which the predetermined breaking area or point is intended to break approximately can lie in the range of a force that can be exerted by an adult person by pressing together a thumb and index finger and/or middle finger.

It is also conceivable that the predetermined breaking area or point can be adapted to break upon applying a rotary motion to the proximal portion of the intermediate section relative to the distal portion of the intermediate section or vice versa.

The breakable section preferably can have the shape of a lip, a web, a rim, a shoulder, a film or the like. Expediently, the breakable section can comprise a tearable film, in particular being made of the same material as the distal and/or the proximal portion of the intermediate section. When applying a force the tearable film can stretch to a limited extent until it finally breaks.

The intermediate section may be formed by injection molding and preferably may consist of an elastically deformable polymer selected from the group comprising polypropylene, cyclic olefin polymer, polyethylene, polyamide, polybutylene terephthalate and polymethyl methacrylate.

It is preferable if the breakable section comprises or is made of a different material than the distal portion and/or the proximal portion of the intermediate section. By choosing a suitable material for the breakable section, the predetermined breaking area or point can be adjusted and adapted to the type of usage of the discharger.

In a preferred embodiment, after breakage of the breakable section, the proximal portion of the intermediate section can be movable relative to the distal portion of the intermediate section along the longitudinal axis between a starting position and a final discharge position. The direction of movement of the proximal portion preferably can be along the longitudinal axis towards the distal end of the discharge section.

A position of the proximal portion of the intermediate section before breakage of the breakable section can be referred to as "initial position". The "starting position" can be defined as a position of the proximal portion of the intermediate section being reached immediately after breakage of the breakable section, i.e. when the proximal portion of the intermediate section can be movable relative to the distal portion. The "final discharge position" can be defined as a position of the proximal portion of the intermediate section in which—once reached by an initial motion of the proximal portion of the intermediate section—no further movement of the proximal portion in its initial direction is possible.

Against this background, the breakable section advantageously also may act in favour of child safety, since it can prevent the proximal portion of the intermediate section from being unintentionally moved along the longitudinal axis in a manner allowing for a discharge of the fluid. At least concerning young children, the provided discharger thus can be regarded as being child-resistant.

However, the discharger can further comprise a securing means or device which can be adapted to prevent the proximal portion of the intermediate section from being unintentionally moved from the starting position along the longitudinal axis.

It is preferred if in the starting position the proximal portion of the intermediate section at least partially can protrude from the distal portion of the intermediate section and preferably can receive the distal portion to be guided through the proximal portion when the proximal portion is being moved towards the distal end of the discharge section and towards the final discharge position.

According to this embodiment, the distal portion of the intermediate section preferably can have an outer diameter essentially equal to or slightly greater than an inner diameter of the proximal portion of the intermediate section, such that the distal portion after breakage of the breakable section can be guided through the proximal portion. For example, the distal portion can have an outer diameter that is between 3 mm and 15 mm, preferably between 6 and 7 mm. The inner diameter of the proximal portion can be up to 0.1 mm or 0.2 mm smaller than the outer diameter of the distal portion. The inner diameter of the separate container can be equal to the inner diameter of the proximal portion or of a part of the proximal portion. The receiving space of the proximal portion can have an inner diameter that is equal to the outer diameter of the separate container, which can be e.g. in the range of 5 mm to 20 mm and is preferably between 8 and 9 mm.

Advantageously, in the initial position of the proximal portion of the intermediate section, i.e. before breakage of the breakable section, the distal portion of the intermediate section can be at least partially enclosed by the proximal portion. However, the distal portion can also be entirely enclosed by the proximal portion.

After the breakage of the breakable section, the distal portion and/or the proximal portion preferably maintain their structure. In other words, the breakage of the breakable section advantageously only "destroys" the breakable section itself but does not change the form or structure of the distal portion and the proximal portion. The breakable section can have a, preferably round or circular, shape that encircles the longitudinal axis.

If the structure of the distal portion and/or the proximal portion is maintained, the distal portion can continue cooperating with the proximal end of the discharge section, after the breakage of the breakable section.

In an embodiment of the discharger, the distal portion of the intermediate section and the proximal end of the discharge section can cooperate by a plug connection. The proximal end of the discharge section preferably can be simply inserted into an opening located at a receiving end of the distal portion and can be maintained in position particularly in a forcelocking manner. An additional interconnection such as gluing or welding, especially laser welding, is not necessarily required, however, can nevertheless be performed.

The cooperation between the proximal end of the discharge section and the distal portion of the intermediate section can also be based on a snap-in connection. In this context, for instance, a locking element, such as a locking pin or the like, may be provided at the distal portion and a counter locking element may be provided at the proximal end. The proximal end of the discharge section then, as it is inserted through the opening into the distal portion of the intermediate section, can slide over the locking element at the distal portion which in cooperation with the counter locking element provided at the proximal end can prevent a sliding off or dropout of the discharge section. Additional interconnection methods like welding or gluing can be omitted.

Another possible type of cooperation between the distal portion of the intermediate section and the proximal end of the discharge section can be a screw connection, wherein the distal portion of the intermediate section preferably may include an internal thread and the proximal end of the discharge section preferably may include an external thread.

Preferably, the distal portion of the intermediate section further can comprise a stop portion serving as a stop for the proximal end of the discharge section when being inserted into the distal portion. In other words, the stop portion can define to what extent the distal end of the discharge section can be inserted into the proximal portion of the intermediate section.

It is particularly preferred if only between one tenth and one twentieth of the entire length of the discharge section can be received into the distal portion of the intermediate section. In this way, the dimensions of the distal portion of the intermediate section can be reduced to a necessary minimum level that allows for holding the proximal end of the discharge section in place. The material consumption thus can be kept down to a minimum.

In a further embodiment of the discharger, the distal portion of the intermediate section can comprise an activation means or device for establishing a flow connection for the fluid from within the receiving space of the proximal portion of the intermediate section to the inlet opening of the discharge section.

One concept of the present disclosure is to avoid a direct storage of the fluid inside the discharger itself. By providing an intermediate section comprising a proximal portion having a receiving space, a separate container containing an amount of fluid to be discharged can be loaded into the discharger. Consequently, a practically unlimited storage life of the discharger itself can be achieved. Moreover, this concept allows for easy and reliable operation of the discharger since the flow connection for the fluid from the container being loaded into the receiving space of the proximal portion of the intermediate section to the inlet opening of the discharge device can be automatically established by the activation device.

Expediently, the flow connection can be established automatically after breakage of the breakable section by moving the proximal portion of the intermediate section relative to the distal portion of the intermediate section along the longitudinal axis from the starting position towards the distal end of the discharge section and towards the final discharge position.

In the initial position, i.e. before breakage of the breakable section, and/or in the starting position of the proximal portion of the intermediate section, the activation device preferably can be inoperative, meaning that no connection to the fluid to be discharged can be established.

Advantageously, the activation device can establish the flow connection when the proximal portion of the intermediate section is on its way between the starting position and the final discharge position so that the fluid can begin to flow through the discharge passage of the discharge section before the proximal portion can reach the final discharge position.

In another embodiment, the activation device can establish the flow connection when the proximal portion of the intermediate section is brought from its initial position to its starting position, i.e. the fluid connection can be established during the breakage of the breakable section.

It is also conceivable that the activation device may require an additional operation step to be performed by a user in order to actually establish the flow connection. However, it is particularly preferred if the flow connection can be established automatically by moving the proximal portion of the intermediate section towards the final discharge position.

In still a further embodiment, the activation device can be positioned at least partially within the proximal portion of the intermediate section so as to protrude into the receiving space and beyond the receiving space when the proximal portion is being moved from the starting position towards the final discharge position. By protruding into the receiving space defined by the proximal portion and further beyond this receiving space, i.e. beyond a receiving end of the proximal portion, the activation device is capable of interacting with the container loaded into the receiving space, for instance by breaking a seal of the container.

In this context, it is preferred that the activation device is provided with an element or means for breaking a seal, in particular for piecing, penetrating, puncturing and/or perforating the seal.

The activation device preferably may comprise a piercing tip having a flow channel for establishing the flow connection for the fluid from the receiving space to the inlet opening of the discharge section. Advantageously, the outer surface of the piercing tip can have a convexly curved, in particular a dome-shaped, configuration and preferably can be rotationally symmetric. The flow channel preferably can be centrally located within the piercing tip, in particular along a rotary axis of the piercing tip. However, the flow channel can also be located at an offset position relative to the rotary axis of the piercing tip. It is particularly preferred that the piercing tip can be rotationally symmetric about the longitudinal axis defined by the discharge section.

According to another embodiment, the piercing tip may comprise a ridge at an apex, wherein the ridge preferably can be perpendicular to the longitudinal axis. The ridge, however, can also be inclined or slanted relative to the longitudinal axis. Expediently, the ridge can be interrupted by the flow channel such that two protrusions adjacent to the flow channel are formed. In other words, the flow channel can divide the ridge into two separated ridge-like protrusions which preferably may have about the same dimensions.

In an embodiment, the activation device can be sealingly fitted within the proximal portion of the intermediate section so as to prevent at least substantially fluid leakage through the receiving end of the distal portion of the intermediate section. In this context, it is particularly preferable if the activation device or the distal portion of the intermediate section comprises a sealing lip or the like providing a seal against an inner wall of the proximal portion of the intermediate section.

Advantageously, the distal portion is adapted to advance inside (i.e. into) the proximal portion after the breakage of the breakable section, wherein a sealing connection is created between the distal portion and the proximal portion. When advancing inside the proximal portion (after the breakage of the breakable section), the distal portion can act as a piston that displaces the fluid stored in the separate container. Due to the sealing connection, an undesired leakage of the container and/or the proximal portion is prevented.

Expediently, the sealing lip, the sealing connection or the like may be provided at the activation means, in particular at the piercing tip, preferably at an outer surface region before the piercing tip starts tapering. The sealing lip may me integrally formed with the activation means which advantageously eliminates the need for separate sealing elements, such as gaskets or O-rings. Thus, an effective concept is provided which ensures that the fluid from the container flows at least substantially only into the inlet opening and through the discharge passage of the discharge device.

In a preferred embodiment, the distal portion of the intermediate section may include a first essentially cylindrical portion protruding from the proximal portion of the intermediate section and a second portion functioning as the activation device. According to this embodiment, the activation device preferably may be entirely enclosed by the proximal portion of the intermediate section. Further, the first cylindrical portion protruding from the proximal portion may comprise the sealing lip. The breakable portion according to this embodiment preferably can have the shape of a web and may be located at a distal end facing away from the receiving space of the proximal portion where the first cylindrical portion of the distal portion starts to protrude.

In a further embodiment, the activation device can be shaped at least approximately complementary to an inner wall portion of the container adapted to be loaded within the receiving space so as to minimize the residual amount of fluid contained within the container when the proximal portion of the intermediate section is in its final discharge position. In other words, an inner contour of the container essentially may be complementary in shape to the activation device being preferably in the shape of a piercing tip.

The expression "essentially", in this context, implies that the shape of the inner wall portion of the container can deviate from an exact complementary shape of the activation means, especially in an area where the activation means may comprise a ridge or ridge-like protrusions, if applicable.

This design allows for a nearly complete discharge of the fluid since the space available for the fluid can be completely filled by the activation device resulting in a nearly complete displacement of the fluid.

The proximal portion of the intermediate section preferably can have a receiving end with an insertion opening, wherein the receiving space can be accessible through the insertion opening. Further, the proximal portion preferably can be adapted to be loaded with the container by sliding the container through the insertion opening into the receiving space. The receiving space preferably may be dimensioned such that the container at least partially protrudes from the proximal portion.

By keeping the part of the container being inserted into the receiving space as small as possible, the use of material can be kept down to a minimum since according to the present invention the container needs no further encasement. In this context, preferably only one third, more preferably only one fourth, in particular only one tenth of the total length of the container may be received into the receiving space defined by the proximal portion of the intermediate section.

Expediently, inside the proximal portion of the intermediate section a transition portion may be provided which serves as a stop for the container being loaded into the receiving space. This transition portion may be in the shape of a shoulder or an abutment and can determine the length with which the container is received into the receiving space.

The container preferably can cooperate with the receiving space of the proximal portion of the intermediate section by a plug connection or a snap-in connection as has previously been described with regard to the discharge section cooperating with the distal portion of the intermediate section.

In an embodiment, the discharger further may comprise the container, in particular in the form of a cartridge or a capsule, wherein the container can include the predetermined amount of fluid to be discharged by the discharger.

The outer shape of the container may be generally cylindrical and the fluid to be discharged preferably can be contained in a fluid reservoir within the container.

Expediently, the fluid inside the container can be protected from environmental influences by a breakable seal, in particular, a barrier foil. The container may have a distal end face at least part of which being formed by a breakable seal.

The seal may be formed by a portion of an outer wall of the container, wherein preferably the seal portion may have a thickness smaller than that of other portions of the wall. Alternatively, the outer wall of the container can define an opening which, after filling the fluid into the container, may be closed by a separate sealing element. The sealing element may be in the form of a foil or a film.

In an embodiment, the discharge section can comprise projections, such as finger flanges, finger rests or finger grips, in particular being moulded on or being integrally formed with the discharge section.

The discharger thus can be used like a common syringe by holding the discharger with one finger at each projection and with the thumb on a proximal end of the container being loaded into the receiving space of the proximal portion of the intermediate section, thereby providing a comfortable single-hand operation of the discharger. The container in this way can be activated like a push button which is to be pressed by a user with her or his thumb while counteracting this pressing actuation by holding the discharge section with two fingers behind the projections.

In this way, an axial force towards the distal end of the discharge section can be applied to the proximal portion of the intermediate section. As a consequence, the breakable section can break and the proximal portion can be transferred into the starting position. By further applying the axial force, the proximal portion together with the container being loaded in the receiving space of the proximal portion can be moved further towards the distal end of the discharge section. Thereby, the activation device of the distal portion of the intermediate section can establish a flow connection for the fluid from within the receiving space to the inlet opening of the discharge section, preferably by breaking the seal located at a distal end face of the container. As the activation device enters into the fluid reservoir of the container, the fluid can be urged out of the container through the discharge passage of the discharge section.

By directly providing the projections on the discharge section, the provision of additional housing parts can be omitted. The rate of material consumption in the production thus is correspondingly low. Moreover, since during operation of the discharger, on the one hand, the discharge section can be pressed against the distal portion of the intermediate section and, on the other hand, the container can be pressed against the proximal portion of the intermediate section, a slip-tight connection between the above-named separate components—discharge section, intermediate section, container—is not necessarily required. This particularly facilitates on-site assembly and handling of the discharger.

In a further embodiment, the discharge section may comprise a distal end portion defining the outlet opening. Preferably, the distal end portion can be formed integrally or can be made as a separate component, such as a spray head, a needle, a brush, a sponge or a pipette, being connectable to the distal end of the discharge section. For large area applications, for instance, a spray head or a sponge can be of advantage, whereas selective applications might require a needle or a plain tube of small diameter.

In another aspect, the present disclosure also relates to the use of a discharger as disclosed herein for discharging a liquid including at least one medical, dental or veterinary agent, wherein in particular the amount of the liquid can lie in the range of 0.1 to 5 ml and preferably can be approximately 0.5 ml.

In general, the volume for the fluid within the container may be dimensioned as desired in according with the respective intended used. The outer shape and the outer dimensions of the container may be the same for different volumes and thus for different quantities of fluid included within the container.

DESCRIPTION OF THE DRAWINGS

The invention will be explained in more detail hereinafter with reference to the drawings.

DETAILED DESCRIPTION OF THE EMBODIMENTS

Figure 1:
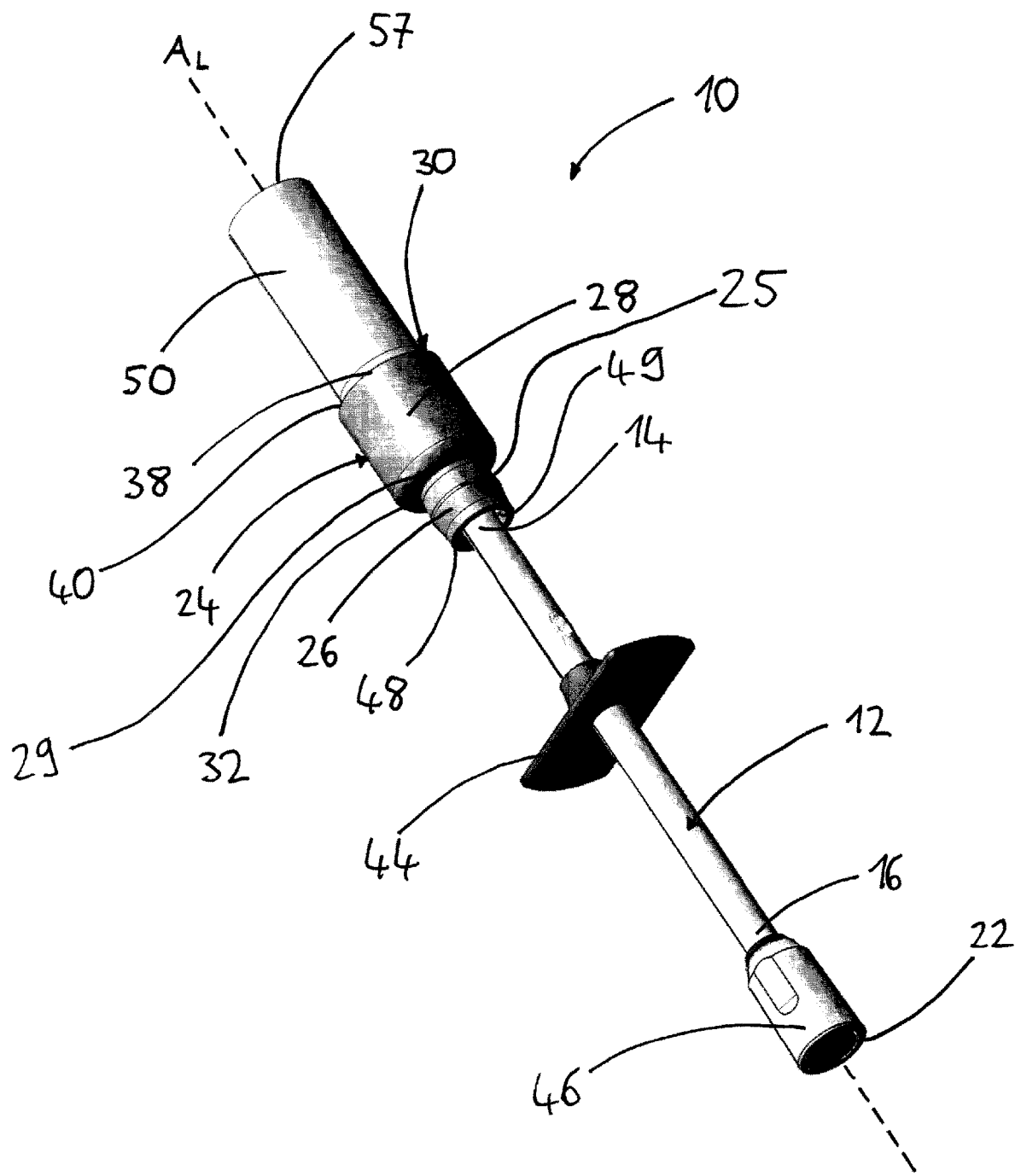
FIG. 1 shows a perspective view of a discharger comprising a container according to the present disclosure.

In the following the same reference numerals will be used for parts having the same or equivalent function. Any statements made having regard to the direction of a component are made relative to the position shown in the drawing and can naturally vary in the actual position of application.

FIG. 1 shows a discharger 10 comprising a discharge section 12 defining a longitudinal axis $A_L$, an intermediate section 24 and a container 50. The discharge section 12 has a proximal end 14 and a distal end 16 and includes wing-like projections 44 being approximately situated in the middle between the proximal end 14 and the distal end 16. The projections 44 are in the shape of a finger flange and, for example, are integrally formed with the discharge section 12 by injection molding. On its distal end 16 the discharge section 12 comprises a distal end portion 46 defining an outlet opening 22. The distal end portion 46 can, for example, be an individual part fixed (e.g. welded) to the discharge section 12, or it can be integrally formed with the discharge section 12, e.g. by injection molding. In this embodiment, the distal end portion 46 is designed as a spray head, preferably for a large area application. However, the distal end portion 46 can be adapted to the type and site of application and can also comprise a needle (cannula), a brush, a sponge, a pipette or the like.

The intermediate section 24 comprises a proximal portion 28 and a distal portion 26 being formed in one piece and being interconnected by a breakable section 32. The breakable section 32 is located at a distal end 29 of the proximal portion 28 and has the shape of a tearable film or a web. The breakable section 32 is made of the same material as the proximal portion 28 and the distal portion 26.

The distal portion 26 of the intermediate section 24 has a receiving end 48 with an opening 49 for receiving the proximal end 14 of the discharge section 12. The proximal end 14 is merely plugged into the distal portion 26 without further securing the connection by welding or gluing.

The proximal portion 28 of the intermediate section 24 also has a receiving end 38 with an insertion opening 40 and defines a receiving space 30 which is adapted to be loaded with a separate container 50. The container has a proximal end 57 and is plugged into the receiving space 30 by sliding the container 50 through the insertion opening 40.

In total, the discharger 10 includes three individual parts, namely the discharge section 12, the intermediate section 24 and the container 50. In general, the distal end portion 46 can be a further individual part, too.

The distal portion 26 of the intermediate section 24 comprises a sealing lip 25 disposed circumferentially around the distal portion 26. The sealing lip 25 is defined by a circumferential area of the distal portion 26 being larger in diameter than the remaining distal portion 26.

Figure 2:
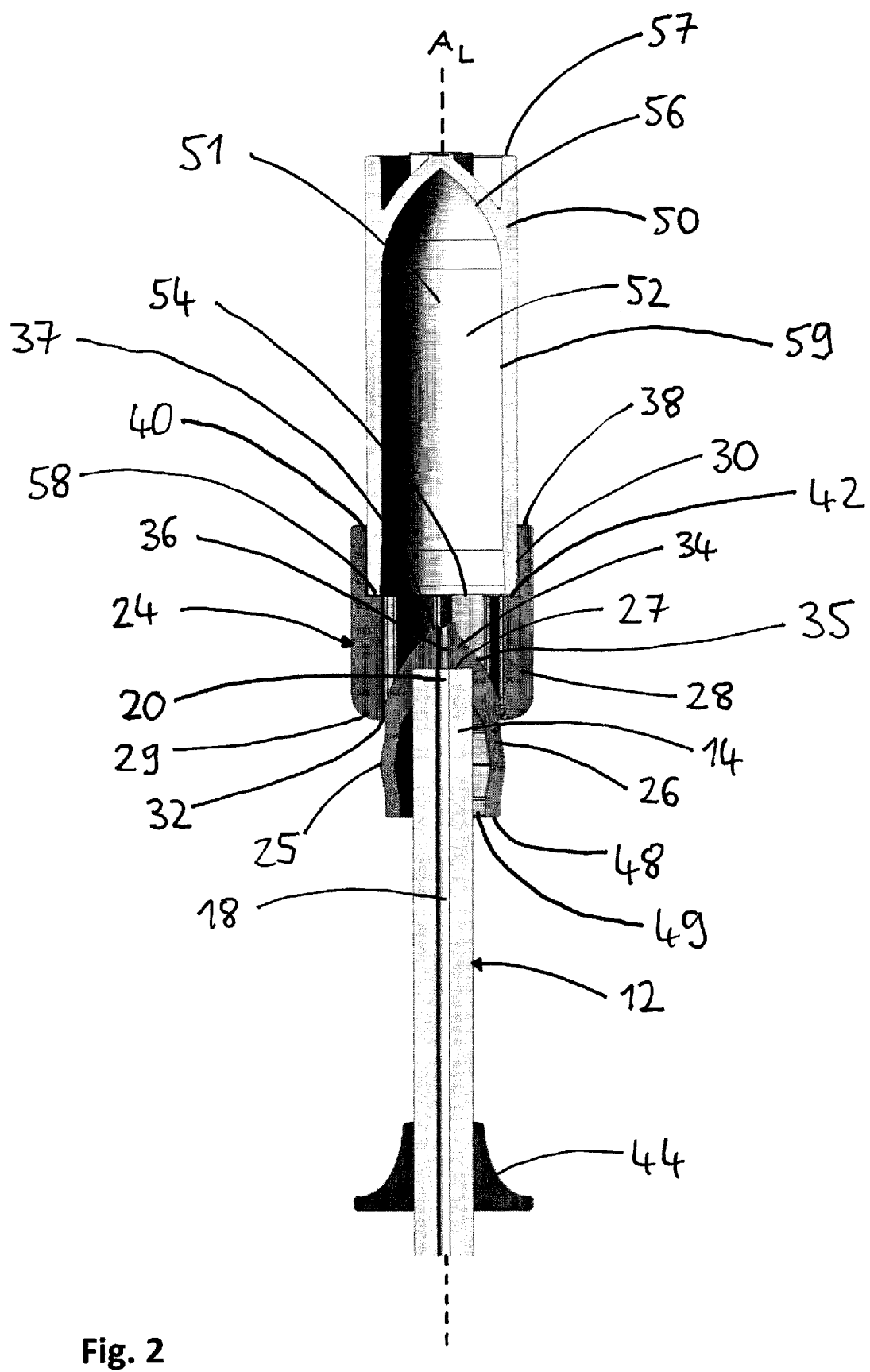
FIG. 2 shows a cross-sectional view along the longitudinal axis of the discharger of FIG. 1.

FIG. 2 shows a cross-sectional view of the discharger 10, wherein for the purpose of improved visualization, the distal end 16 as well as the distal end portion 46 of the discharge section 12 have been omitted.

FIG. 2 reveals that the distal portion 26 of the intermediate section 24 further comprises an activation means or device 34 enclosed by the proximal portion 28 of the intermediate section 24. The activation device 34 is in the shape of a piercing-tip having a dome-shaped contour 35 being essentially complementary to an inner wall portion 56 of the container 50. The activation device 34 further comprises a flow channel 36 providing a flow connection to an inlet opening 20 of a discharge passage 18 centrally running inside the discharge section 12 along the longitudinal axis $A_L$. The flow channel 36 is centrally located within the dome-shaped activation device 34 and further comprises two separated deformable ridge-like protrusions 37 located adjacent to an entry opening of the flow channel 36. The flow channel 36 extends along the longitudinal axis $A_L$.

FIG. 2 moreover reveals that the container 50 comprises a fluid reservoir 51 holding an amount of fluid 52 to be discharged. The container 50 further comprises a distal end face 58 formed by a breakable seal 54. The inner wall portion 56 of an inner wall 59 of the container 50 is rotationally symmetric and approximately complementary to the dome-shaped contour 35 of the activation device 34.

In addition, it can be seen that the receiving space 30 is defined by an area between the receiving end 38 and a transition portion 42 serving as a stop for the container 50 when being loaded into the receiving space 30. Only roughly one seventh of the total length of the container 50 is received in the receiving space 30. The rest of the container 50 protrudes from the receiving end 38 of the proximal portion 28.

Figure 3:
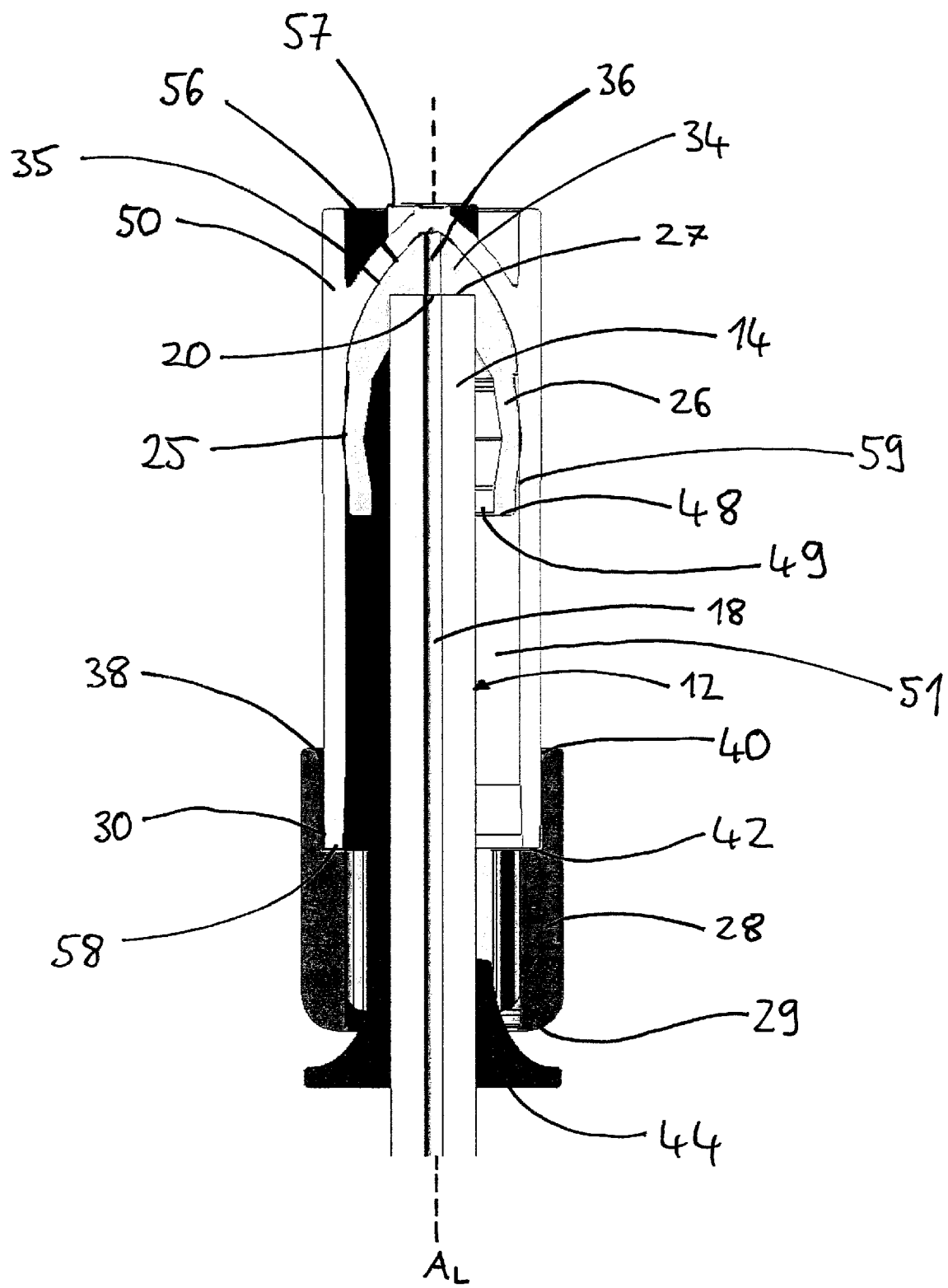
FIG. 3 shows the discharger of FIG. 2 with the proximal portion of the intermediate section in the final discharge position.

FIG. 3 shows the discharger 10 with the proximal portion 28 in its final discharge position, i.e. the proximal portion 28 has been fully moved towards the distal end 16 (cf. FIG. 1) of the discharge section 12. In this position, the breakable section 32 (cf. FIGS. 1 and 2) is broken and the distal portion 26 of the intermediate section 24 is located in the fluid reservoir 51 of the container 50. The seal 54 has been pierced and the fluid 52 has been displaced by the activation device 34. The deformable ridge-like protrusions 37 (cf. FIG. 2) have been compressed such that the activation device 34 and the inner wall portion 56 of the container 50 establish a form-fitting connection.

It can be further seen, that the sealing lip 25 of the distal portion 26 tightly fits to the inner wall 59 of the container 50, thereby preventing fluid leakage of the container 50 past the receiving end 48 of the distal portion 26. The complementary shapes of the inner wall portion 56 of the container 50 and the contour 35 of the activation device 34 ensure that virtually no residual amounts of fluid 52 remain within the container 50.

For operating the discharger 10, i.e. to discharge the fluid 52 inside the container 50 through the discharge passage 18 out of the outlet opening 22, the proximal portion 28 together with the container 50 protruding from the receiving end 38 needs to be pushed towards the distal end 16.

When the proximal portion 28 is in an initial position as shown in FIGS. 1 and 2, the breakable section 32 is still intact and the activation device 34 is still positioned spaced apart from the seal 54 of the container 50. In other words, the activation device 34 does not yet protrude into the fluid reservoir 51 of the container 50.

When applying an axial force to the proximal portion 28 of the intermediate section 24 by actuating the proximal end 57 of the container 50 like a push button which can be pushed by the user with a thumb while counteracting this actuation by holding the projections 44 with two fingers behind these projections 44, in a first step, the breakable section 32 breaks and the proximal portion 28 is transferred into its starting position. In the starting position the proximal portion 28 is moveable relative to the distal portion 26 along the longitudinal axis $A_L$ towards the distal end 16 of the discharge section 12. In a second step, for discharging the fluid 52 the user has to deliberately push the container 50 towards the distal end 16.

In general, the movement of the proximal portion 28 between the initial position and the starting position and further towards the final discharge position preferably can be adapted to be a flowing movement, such that the fluid can be discharged uniformly.

While the proximal portion 28 together with the container 50 moves towards the distal end 16, the deformable ridge-like protrusions 37 initially punctuate the seal 54 while the dome-shaped activation device 34 then pierces the seal 54. The activation device 34 enters into the fluid reservoir 51 of the container 50, thereby urging the fluid 52 out of the container 50 through the flow channel 36 being connected to the discharge passage 18. Due to the complementary shapes of the activation device 34 and the inner wall portion 56 of the container 50 the fluid 52 can only escape through the flow channel 36. Since the distal portion 26 sealingly fits into the fluid reservoir 51 by the sealing lip 25, leakage of fluid past the distal portion 26 is prohibited at any time.

In general, the discharger 10 may be fabricated from any suitable material. Preferably, the material can be plastic. The material may be selected from the group comprising polypropylene, cyclic olefin polymer, polyethylene, polyamide, polybutylene terephthalate and polymethyl methacrylate. Alternatively, the material may be glass, metal or an alloy.

It is particularly preferred that the discharger 10, i.e. each of the container 50, the intermediate section 24 and the discharge section 12, may be fabricated by injection molding as injection-molded part.

With respect to one common classification applied in the medical, dental or veterinary field or the health care sector, the discharger as provided by the present disclosure belongs to the group consisting of systems without projection cap.

The invention claimed is:

1. A discharger for discharging a predetermined amount of fluid from a separate container, comprising:
   a discharge section defining a longitudinal axis and having a proximal end and a distal end and having a discharge passage for the fluid extending between an inlet opening and an outlet opening of the discharge section; and
   an intermediate section comprising a distal portion engaging the proximal end of the discharge section and a proximal portion defining a receiving space configured to be loaded with the separate container holding an amount of the fluid to be discharged by the discharger, the distal portion and the proximal portion being formed in one piece and are interconnected by a breakable section, and after breakage of the breakable section, the distal portion is configured to act as a piston configured to displace the fluid in the separate container.

2. The discharger according to claim 1, wherein the breakable section comprises a predetermined breaking area configured to break upon applying an axial force to the intermediate section.

3. The discharger according to claim 1, wherein after breakage of the breakable section the proximal portion of the intermediate section is movable relative to the distal portion of the intermediate section along the longitudinal axis between a starting position and a final discharge position.

4. The discharger according to claim 3, wherein in the starting position, the proximal portion of the intermediate section at least partially protrudes from the distal portion of the intermediate section and receives the distal portion to be guided through the proximal portion when the proximal portion is being moved towards the distal end of the discharge section and towards the final discharge position.

5. The discharger according to claim 3, wherein the distal portion of the intermediate section comprises an activator configured to establish a flow connection for the fluid from within the receiving space of the proximal portion of the intermediate section to the inlet opening of the discharge section.

6. The discharger according to claim 5, wherein the flow connection is established automatically after breakage of the breakable section by moving the proximal portion of the intermediate section relative to the distal portion of the intermediate section along the longitudinal axis from the starting position towards the distal end of the discharge section and towards the final discharge position.

7. The discharger according to claim 6, wherein the activator is configured to not enable the flow connection for the fluid from within the receiving space of the proximal portion of the intermediate section to the inlet opening of the discharge section before breakage of the breakable section or in the starting position.

8. The discharger according to claim 7, wherein the activator is positioned at least partially inside the proximal portion of the intermediate section so as to protrude into the receiving space and beyond the receiving space when the proximal portion is being moved from the starting position towards the final discharge position.

9. The discharger according to claim 5, wherein the activator is sealingly fitted within the proximal portion of the intermediate section so as to prevent at least substantial fluid leakage through the breakable section after breakage.

10. The discharger according to claim 5, wherein the activator is shaped at least approximately complementary to an inner wall portion of the container configured to be loaded within the receiving space so as to minimize a residual amount of the fluid contained within the container when the proximal portion of the intermediate section is in the final discharge position.

11. The discharger according claim 1, wherein the proximal portion of the intermediate section has a receiving end with an insertion opening, the receiving space being accessible through the insertion opening, the proximal portion is configured to be loaded within the container by enabling the container to be slid through the insertion opening into the receiving space and the receiving space is dimensioned such that when loaded, the container at least partially protrudes from the proximal portion.

12. The discharger according to claim 11, wherein inside the proximal portion of the intermediate section a transition portion is provided which serves as a stop for the container being loaded into the receiving space.

13. The discharger according to claim 1, further comprising the container, the container including the predetermined amount of fluid to be discharged by the discharger.

14. The discharger according to claim 1, wherein the discharge section comprises projections.

15. A method comprising:
   operating a discharger according to claim 1 to discharge the fluid, the fluid including at least one medical, dental or veterinary agent the amount of the fluid lying in the range of 0.1 to 5 ml.

16. The discharger according to claim 1, wherein the container is a cartridge or a capsule, the container including a predetermined amount of the fluid to be discharged by the discharger, the container having a generally cylindrical outer shape, and the fluid inside the container being protected from environmental influences by a breakable seal or the container has a distal end face at least a part of which being formed by the breakable seal.

17. The discharger according to claim 1, wherein the discharge section comprises projections molded on or being integrally formed with the discharge section.

18. The method of claim 15, wherein the amount of the fluid is approximately 0.5 ml.

* * * * *